United States Patent [19]
Fujishima et al.

[11] Patent Number: 4,614,719
[45] Date of Patent: Sep. 30, 1986

[54] PROCESS FOR PRODUCING RIBAVIRIN

[75] Inventors: Tetsuro Fujishima; Yoshiomi Yamamoto, both of Choshi, Japan

[73] Assignee: Yamasa Shoyu Kabushiki Kaisha, Chiba, Japan

[21] Appl. No.: 489,409

[22] Filed: Apr. 26, 1983

[30] Foreign Application Priority Data

Apr. 30, 1982 [JP] Japan ................................ 57-73895
Jun. 11, 1982 [JP] Japan ............................... 57-100832
Jul. 5, 1982 [JP] Japan ............................... 57-117385

[51] Int. Cl.$^4$ ............................................. C12P 19/28
[52] U.S. Cl. ...................................... 435/85; 435/193; 435/840
[58] Field of Search .................. 435/84, 85, 193, 840, 435/843, 830, 822, 911, 824, 832, 828, 847, 848, 850, 852, 859, 874, 880, 873, 849, 882, 909, 921, 910

[56] References Cited

U.S. PATENT DOCUMENTS 4,458,016 7/1984 Yamanaka et al. .................. 435/85

FOREIGN PATENT DOCUMENTS 146593 9/1982 Japan .

OTHER PUBLICATIONS

Fujishima et al., Chemical Abstracts, vol. 100, #50053y.
Furuya et al., Chemical Abstracts, vol. 84, 1976, #42018b.
Ochiai et al., Chemical Abstracts, vol. 84, 1977, #15189t.

Primary Examiner—Sam Rosen
Assistant Examiner—William J. Herald
Attorney, Agent, or Firm—Wenderoth, Lind & Ponack

[57] ABSTRACT

There is disclosed a process for producing ribavirin from 1,2,4-triazole-carboxamide and a ribose donor by the enzymatic action of a microorganism belonging to specific genera, e.g. Brevebacterium. The specific feature of the invention is, above all, utilization of said microorganism under non-proliferatating conditions.

7 Claims, No Drawings

PROCESS FOR PRODUCING RIBAVIRIN

BACKGROUND OF THE INVENTION

1. Technical Field

This invention relates to an enzymatic process for producing ribavirin.

The chemical nomenclature of ribavirin is 1-β-D-ribofuranosyl-1,2,4-triazole-3-carboxamide, which is also known as virazole (trade name), and it is known as a compound having a broad and potent antiviral activity against DNA and RNA viruses [Annals of the New York Academy of Sciences 284, 272–292 (1977)].

2. Prior Art

The processes for producing ribavirin known in the art may be classified into synthetic methods, fermentative methods and enzymatic methods.

Representatives of synthetic methods known include methods in which 3-methoxycarbonyl-1,2,4-triazole is caused to react with 1-O-acetyl-2,3,5-tri-O-acyl-β-D-ribofuranose, and the resultant 1-(2',3',5'-tri-O-acyl-β-D-ribofuranosyl)-3-methoxy-carbonyl-1,2,4-triazole is treated with ammonia to effect amidation and deblocking thereof (see Japanese Patent Laid-open Nos. 4469/1973, 80070/1974 and 80071/1974); the method similar to the aforementioned in which an aralkyloxyl group is employed as the substituent at the 3-position of the triazole (see Japanese Laid-open Patent Application No. 160793/1980); methods in which 3-methoxycarbonyl-1,2,4-triazole is trimethylsilylated and caused to react with a halide of 2,3,5-tri-O-benzoyl-β-D-ribofuranoside, followed by treatment with ammonia (see Japanese Patent Laid-Open Nos. 4469/1973 and 86372/1974); and others. In any of these synthetic methods, it would be required to block the active groups of the starting compounds before the reaction, or sometimes activation of the ribose may be required in carrying out the reaction. In some cases, heating to a high temperature would also be necessary. Further, after the reaction, deblocking and amidation must be performed, thus involving the problems of cumbersome reaction operations. As another problem, the positional selectivity during the condensation reaction is not high in any one of these methods as far as the present inventors are concerned.

Fermentative methods known in the art include methods in which 1,2,4-triazole-3-carboxamide is added at a time or intermittently to a culture medium containing carbon sources, nitrogen sources, inorganic substances and other nutrients necessary for cultivation of a microorganism employed before initiation of culturing or during culturing of a microorganism belonging to the genus Brevibacterium, the genus Corinebacterium, the genus Arthrobacter, the genus Micrococcus or the genus Bacillus, and cultivation is carried out for a period of time of 2 to 8 days after initiation of culturing, thereby to form and accumulate ribavirin in the culture medium [see Japanese Patent Publication No. 17830/1979; Journal of The Agricultural Chemical Society of Japan, 50 (9), 423–430 (1976)]. This method could involve following problems: (1) since production of ribavirin is carried out in a nutrient medium during proliferation of microorganisms, it is first necessary to prepare a culture medium containing various nutrient sources for proliferation of microorganisms, and cumbersome pre-treatments such as sterilization of the medium before inoculation of the seed microorganisms are also necessary; (2) cultivation for the purpose of accumulation of ribavirin, which is accompanied with proliferation of microorganisms, is carried out generally at a normal temperature of 20° to 40° C. and therefore it is constantly required to take care about contamination with miscellaneous microorganisms. Moreover, under such conditions, there also exists an activity for decomposing the ribavirin, thus lowering the yield of this objective compound; (3) proliferation of microorganisms must be carried out for a long period of time of 2 to 8 days; (4) various nucleosides, phosphorylated products of ribavirin and other metabolites are formed as by-products, and for recovery of ribavirin from the culture broth thus requires that ribavirin be separated not only from the starting compounds but also from various by-products, whereby isolation and purification are rendered cumbersome; and (5) microorganisms must be cultured each time in production of ribavirin.

Enzymatic methods known in the art include methods in which 1,2,4-triazole-3-carboxamide is caused to react with ribose-1-phosphate at a pH of 5–9 and at a temperature of 0°–50° C. in the presence of a nucleoside-phosphorylase [see Japanese Patent Laid-open No. 29720/1975]. The method could have problems that the ribose-1-phosphate used as a ribose donor is unstable and is not easily available, and that a preparation of the purified enzyme which is used is not easy to be prepared.

SUMMARY OF THE INVENTION

The present inventors have found for the first time that ribavirin can be produced by the enzymatic reaction with the use of a culture of a microorganism, intact cells of a microorganism or a modification of microorganism cells as an enzyme source under non-proliferating conditions of the microorganism.

The present invention provides a process for producing ribavirin which comprises causing 1,2,4-triazole-3-carboxamide or a salt thereof and a ribose donor to contact in the presence of an enzyme source based on a microorganism belonging to the genus selected from the group shown below and containing an enzyme which catalyzes the reaction to form ribavirin from 1,2,4-triazole-3-carboxamide and a ribose donor under non-proliferating conditions of the microorganism concerned in an aqueous medium to form ribavirin therein and recovering the ribavirin formed from the medium: (1) the genus Brevibacterium; (2) the genus Corynebacterium; (3) the genus Arthrobacter; (4) the genus Micrococcus; (5) the genus Bacillus; (6) the genus Flavobacterium; (7) the genus Microbacterium or Brochothrix; (8) the genus Xanthomonas; (9) the genus Pseudomonas or Alteromonas; (10) the genus Achromobacter; (11) the genus Escherichia; (12) the genus Aerobacter; (13) the genus Sarcina; (14) the genus Staphylococcus; (15) the genus Bacterium; (16) the genus Serratia; (17) the genus Proteus; (18) the genus Cellulonomas; (19) the genus Enterobacter; (20) the genus Mycoplana; (21) the genus Vibrio; (22) the genus Erwinia; (23) the genus Klebsiella; (24) the genus Aeromonas; (25) the genus Mycotorula; and (26) the genus Candida.

In the present invention, "an enzyme source based on a microorganism" means a culture of the microorganism, intact cells of the microorganism or a modification of cells of the microorganism.

The most significant difference between the present invention and the prior fermentative and enzymatic methods resides in the fact that, in the present invention, a culture of a microorganism, intact cells of a microorganism, or a modification of cells of a microorganism is used as an enzyme preparation and 1,2,4-triazole-3-carboxamide or its salt and a ribose donor are caused to react under such a condition that the microorganism, does not proliferate whereby the enzymatic reaction is optimized.

The present invention has such advantages over the prior fermentative methods that (1) reaction at an elevated temperature, which is an example of the reaction under non-proliferating conditions of a microorganism, can reduce contamination of the reaction mixture with undesired microorganisms to the minimum and reduce decomposition of ribavirin once produced with no reduction of the ribavirin yield; (2) the reaction involved is enzymatic, and the reaction time required is thus shorter and formation of by-products is less which in turn results in easier purification required; (3) repetitious or continuous use of the enzyme source is possible; and (4) it is possible to store the enzyme source and production or use of the enzyme source can thus be done any time. Further, the present invention has such advantages over the prior enzymatic method that (1) it is easy to prepare the enzyme source; and (2) the ribose donor is readily available since it is selected from a wide variety of materials such as nucleosides and nucleotides. The present invention, when a suitable enzyme source is used, can produce ribavirin in a far higher yield than the prior methods.

DETAILED DESCRIPTION OF THE INVENTION

Enzyme source

The enzyme source to be used in the present enzymatic reaction is, as described hereinabove, one based on a microorganism and is a culture of the microorganism, intact cells of the microorganism or a modification of cells of the microorganism.

Microorganisms employed

The microorganisms to be employed in the present invention are those of which cultures, intact cells or modifications of cells contain an enzyme capable of catalyzing the reaction between 1,2,4-triazole-3-carboxamide and a ribose donor to form ribavirin, more specifically including microorganisms belonging to the genus Brevibacterium, the genus Corynebacterium, the genus Arthrobacter, the genus Micrococcus, the genus Bacillus, the genus Flavobacterium, the genus Microbacterium or Brochothrix, the genus Xanthomonas, the genus Pseudomonas or Alteromonas, the genus Achromobacter, the genus Escherichia, the genus Aerobacter, the genus Sarcina, the genus Staphylococcus, the genus Bacterium, the genus Serratia, the genus Proteus, the genus Cellulomonas, the genus Enterobacter, the genus Mycoplana, the genus Vibrio, the genus Erwinia, the genus Klebsiella, the genus Aeromonas, the genus Mycotorula, or the genus Candida, and having the aforesaid activity. In the present invention, the microorganism strains are not particularly limited in species, so long as they have such basic properties.

In the following, there are set forth examples of microorganism strains easily available to those skilled in the art.

(1-1) *Brevibacterium acetylicum* AT-6-7 FERM P-6305 (ATCC 39311)
(1-2) *Brevibacterium imperiale* ATCC 8365
(2-1) *Corynebacterium equi* IAM 1038
(3-1) *Arthrobacter citreus* IFO 12957 (ATCC 11624)
(3-2) *Arthrobacter globiformis* IFO 12137 (ATCC 8010)
(4-1) *Micrococcus luteus* ATCC 4698 (IAM 1056)
(4-2) *Micrococcus varians* IFO 3765 (ATCC 399)
(4-3) *Micrococcus roseus* IFO 3768 (ATCC 186)
(5-1) *Bacillus subtilis* ATCC 14593
(5-2) *Bacillus cereus* IAM 1029
(6-1) *Flavobacterium arborescens* IFO 3750 (ATCC 4358)
(6-2) *Flavobacterium lutescens* IFO 3084 (IAM 1667) (ATCC 25311)
(6-3) *Flavobacterium lutescens* IFO 3085
(7-1) *Microbacterium thermosphactum* IFO 12167 (*Brochothrix thermosphacta* ATCC 11509)
(8-1) *Xanthomonas oryzae* IFO 3312 (*Xanthomonas campestris* ATCC 21754)
(9-1) *Pseudomonas putrefaciens* IFO 3908 (*Alteromonas putrefaciens* ATCC 8071)
(9-2) *Pseudomonas putrefaciens* IFO 3909 (*Alteromonas putrefaciens* ATCC 8072)
(9-3) *Pseudomonas putrefaciens* IFO 3910 (*Alteromonas putrefaciens* ATCC 8073)
(9-4) *Pseudomonas schuylkilliensis* IAM 1051
(9-5) *Pseudomonas ovalis* IAM 1002
(9-6) *Pseudomonas dacunhae* IAM 1089
(10-1) *Achromobacter parvulus* IFO 13182 (NRRL B-2395)
(10-2) *Achromobacter xerosis* IFO 12668
(11-1) *Escherichia coli* IFO 3301
(11-2) *Escherichia coli* IAM 1268 (ATCC 11303)
(12-1) *Aerobacter aerogenes* IAM 1019

This microorganism strain was deposited at the Fermentation Research Institute, Agency of Industrial Science & Technology (hereinafter referred to as FERM), Yatabe-machi, Ibaragi, Japan, on May 24, 1982, under the deposition number of FERM P-6538.

(13-1) *Sarcina marginata* IAM 1130

This microorganism strain was deposited at FERM on May 24, 1982, under the deposition number of FERM P-6539.

(14-1) *Staphylococcus aureus* IAM 1011 (ATCC 6538 P)
(14-2) *Staphylococcus aureus* IFO 3060
(15-1) *Bacterium succinicum* IAM 1017

This microorganism strain was deposited at FERM on May 24, 1982, under the deposition number of FERM P-6540.

(16-1) *Serratia marcescens* IAM 1105
(17-1) *Proteus vulgaris* IAM 1025
(18-1) *Cellulomonas flavigena* IFO 3753
(18-2) *Cellulomonas flavigena* IFO 12680 (ATCC 486)
(19-1) *Enterobacter aerogenes* IFO 12010
(19-2) *Enterobacter cloacae* ATCC 7256
(20-1) *Mycoplana bullata* IFO 13290 (ATCC 4278)
(21-1) *Vibrio anguillarum* IFO 13266 (ATCC 19264)
(22-1) *Erwinia carotovora* subsp. *carotovora* IFO 12380
(23-1) *Klebsiella pneumoniae* ATCC 8308
(24-1) *Aeromonas hydrophila* subsp. *anaerogenes* IFO 13282 (ATCC 15467)
(25-1) *Mycotorula japonica* OUT 6226
(26-1) *Candida polymorpha* IFO 0836

This microorganism strain was deposited at FERM on May 24, 1982, under the deposition number of FERM P-6541.

In the deposition numbers of the above microorganism strains, those attached with ATCC indicate deposition numbers at The American Type Culture Collection, 12301 Parklawn Drive, Rockville, Md., U.S.A., those attached with IFO deposition numbers at the foundation Institute for Fermentation, Osaka, 17-85, Juso-honmachi 2-chome, Yodogawa-ku, Osaka, Japan, those attached with IAM deposition numbers at Institute of Applied Microbiology, University of Tokyo, Yayoi 1-1-1, Bunkyo-ku, Tokyo, Japan, and those attached with OUT deposition numbers at Faculty of Engineering, Osaka University, Yamada-ue, Suita, Japan, respectively. The strains bearing ATCC numbers are stock cultures listed in American Type Culture Collection, Catalogue of Strains I, Fifteenth Edition, 1982. The strains bearing IFO, OUT and IAM numbers are stock cultures listed in JFCC Catalogue of Cultures, 1979, Third Edition or Institute for Fermentation Osaka, List of Cultures 1978, Sixth Edition. The names of the genus and the species to which these microorganisms as stock cultures belong may be changed due to the change in taxonomical standards, but even such microorganism strains are deemed to be identical with those as exemplified above, so long as they have the bacteriological properties which are the same as or equivalent to those as exemplified above.

The mutant strains derived from the above microorganism strains through induced mutation according to the mutagenic methods in general by a physical treatment such as irradiation of UV-ray, X-ray or γ-ray or a chemical treatment with nitrosoguanidine or other mutagens or natural mutation attributable to natural causes may be also available in the present invention, so long as they do not lose the enzymatic activity participating in production of ribavirin.

Further, when the gene for the enzyme participating in production of ribavirin which is the object of the present invention obtained from the microorganism strains preferably used in the present invention as described above is integrated in a microorganism other than the above genera and phenotypically expressed, the method of employing the culture, the intact cells of such a microorganism or the modification thereof for the object of the present invention may also be included within the present invention.

Among the various microorganism strains, the most preferable strain is *Brevibacterium acetylicum* AT-6-7 strain isolated from the soil in the baseball ground of Koshien, Nishinomiya-Shi, Hyogo-Ken, Japan. This strain has the following bacteriological properties.

A. Morphology
  (1) Form and size of cells: short rod-shaped, (0.8–1.0)×(1.0–1.2) μm);
  (2) Formation of spores: none
  (3) Gram staining: positive
B. Growth on various culture media
  (1) Bouillon-agar plate culture (28° C., 48 hours)
    ① Form of colony: circular
    ② Raising of colony surface: flat, smooth
    ③ Size: 2–4 mm
    ④ Color tone: yellow to pinkish yellow
  (2) Bouillon-agar slant culture (28° C., 48 hours)
    ① Growth: good
    ② Form of growth: echinulate
  (3) Bouillon liquid culture (28° C., 48 hours)
    Growth: formation of ring on the surface, sediment slightly formed.
  (4) Bouillon-gelatin stab culture (20° C., 6 days): liquefied in stratiform
  (5) Litmus-milk culture medium (28° C., 4 days): slightly coagulated, peptonization also observed
C. Physiological properties
  (1) Reduction of nitrate (28° C., 5 days): no reductivity
  (2) Formation of hydrogen sulfide (28° C., 5 days): not formed
  (3) Hydrolysis of starch: hydrolyzable
  (4) Catalase: positive
  (5) Indole formation: not formed
  (6) Ammonia formation from peptone and arginine: negative
  (7) Methyl Red test: negative
  (8) V-P test: positive
  (9) Attitude to oxygen: aerobic
  (10) O-F test (by the Hugh Leifson method): F type (Fermentation)
  (11) Acid formation from sugars positive: glucose, mannose, fructose, maltose, saccharose, trehalose; negative: arabinose, xylose, galactose, lactose sorbitol, inositol, glycerine
  (12) Growth pH range: pH 6.0–9.0
  (13) Optimum growth temperature: 25°–37° C.

The above bacteriological properties were examined with reference to the taxonomical standards in Bergey's Manual of Determinative Bacteriology, 7th edition (1957). As the result, the AT-6-7 strain, which is a short-rod bacterium almost approximate to a coccus, forms no filament and forms acids from carbohydrates, was identified to be a strain belonging to the genus Brevibacterium and designated as *Brevibacterium acetylicum* AT-6-7.

The above microorganism strain, *Brevibacterium acetylicum* AT-6-7, was identified according to Bergey's Manual of Bacteriology, 7th edition, and it is possible that they may be identified to belong to other species or genus according to different taxonomical standards due to some changes in taxonomical standards. However, the microorganisms as designated above can be unequivocally specified based on the deposition at the depositories mentioned above and the aforesaid bacteriological properties.

*Brevibacterium acetylicum* AT-6-7 strain was deposited at FERM on January 13, 1982, (FERM P-6305), and the strain delivered directly from FERM to ATCC has acquired the deposition number of ATCC 39311 on Mar. 2, 1983.

Among various microorganism strains as set forth above, those capable of giving ribavirin yields of 50% or more are preferred. Such microorganism strains are as follows:
*Brevibacterium acetylicum* AT-6-7: FERM P-6305 (ATCC 39311)
*Flavobacterium lutescens*: IFO 3084 (ATCC 25311)
*Xanthomonas oryzae:* IFO 3312
*Pseudomonas putrefaciens:* ATCC 8072
*Achromobacter xerosis:* IFO 12668
*Escherichia coli:* IAM 1268 (ATCC 11303)
*Cellulomonas flavigena:* IFO 12680 (ATCC 486)
Among them, *Brevibacterium acetylicum* AT-6-7 is most preferred.

Cultivation

In cultivation of these microorganisms for preparation of the enzyme source, the culture medium and the method of culture employed are not particularly limited, so far as growth of these microorganisms can be permitted.

As a culture medium, there may be employed one containing appropriate amounts of carbon sources and nitrogen sources assimilable by these microorganisms, optionally added with inorganic salts, growth factors, defoaming agents, etc. More specifically, as carbon sources, there may be employed one or more material selected suitably in view of assimilability by the microorganism employed from carbon sources in general, including sugars such as glucose, fructose, maltose, galactose, ribose, saccharose, starch, starch hydrolysate, molasses, waste molasses, etc. or derivatives threof such as fatty acid esters thereof, natural carbohydrates such as wheat, wheat bran, rice, etc., alcohols such as glycerol, mannitol, methanol, ethanol, etc., fatty acids such as gluconic acid, pyruvic acid, acetic acid, citric acid, etc., hydrocarbons such as normal paraffins, kerosin, etc., amino acids such as glycine, glutamic acid, glutamine, alanine, asparagine, etc., and so on. As nitrogen sources, there may be employed one kind or more kinds selected suitably in view of assimilability by the microorganism employed from nitrogen sources in general, including organic nitrogenous materials such as meat extract (bouillon), peptone, yeast extract, dry yeast, soybean hydrolysate, soybean powder, milk casein, casamino acid, various amino acids, corn steep liquor, cotton seed meal or its hydrolysate, fish meal or its hydrolysate, hydrolysates of other animals, vegetables, microorganisms, etc., inorganic nitrogen compounds such as ammonia, ammonium salts such as ammonium nitrate, ammonium sulfate, ammonium chloride, ammonium phosphate, ammonium carbonate, ammonium acetate and the like, nitrates such as sodium nitrate, urea, and so on. Further, as inorganic salts, there may suitably be added one or more of minute amounts of phosphates, chlorides, sulfates, carbonates, nitrates, acetates and other salts of magnesium, manganese, iron, zinc, copper, sodium, calcium, potassium, etc. If necessary, there may also be added a defoaming agent such as a vegetable oil or a surfactant, a minute amount of a growth factor such as vitamins B1, B2, nicotinic acid, pantothenic acid, biotin, p-aminobenzoic acid, etc. When employing a microorganism exhibiting nutrient requirements, substances necessary for its growth must be added into the culture medium as a matter of course.

Cultivation may be performed in a liquid medium containing the above culture medium components by selecting a culture method suitable for the microorganism employed from conventional culture methods such as shaking culture, aerating stirring culture, stationary culture, continuous culture and others.

The cultural conditions may be suitably chosen depending on the microorganism and the culture medium employed, but generally by adjusting pH before start-up of cultivation at about 6 to 8 and carrying out cultivation under the temperature condition of about 25° to 35° C. The culture duration may be a period sufficient for growth of the microorganism employed, being generally 1 to 3 days.

Particulars of enzyme source

The enzyme source used in the present invention comprises an enzyme which catalyzes the reaction of 1,2,4-triazol-3-carboxamide with a ribose donor to produce ribavirin. The enzyme essentially used in the enzymatic reaction in accordance with the present invention is mainly a nucleosidephosphorylase, and the enzyme source used in the present invention must essentially have this enzymatic activity. In addition, when a compound, which can not directly be a substrate of nucleoside phosphorylase is employed as a ribose donor, the enzyme source should preferably have an enzymatic activity for converting the ribose donor into a substrate of the enzyme. The ribose donor is essential but need not be added to the enzymatic reaction system as such, and in such an embodiment the enzyme source must comprise a ribose donor or a metabolic activity producing a ribose donor.

After culturing the microorganism as described above, the culture, the intact cells of the microorganism collected from the culture according to a conventional method such as centrifugation, sedimentation separation, agglomeration separation, or a modification of cells of microorganism obtained by applying a suitable treatment on the intact cells may be used as the enzyme source in the present invention. The term "culture" herein refers to a product under the state where the culture medium and the cultured microbial cells after cultivation are still unseparated from each other. The term "modification of cells" of microorganism refers to dried microbial cells, microbial cells having denatured cell membrane and/or wall, crushed microbial cells, immobilized microbial cells, extract of microbial cells, protein fractions of the microbial cell extract having an enzyme activity participating in production of ribavirin intended by the present invention or purified product thereof, or immobilized product of the protein fractions or purified product thereof, and the like.

Methods for obtaining the modification of microbial cells are to be illustrated below. That is, modifications of microbial cells can be obtained by (1) applying on intact microbial cells singly or in combination physical treatment means such as freeze-thaw treatment, lyophilization, air-drying, acetone-drying, heating under acidic or alkaline conditions, grinding, ultrasonic treatment, osmotic treatment, etc. or chemical or biochemical treatments such as enzymatic treatments with lysozyme, cell wall lysis enzymes, etc., contact treatments with solvents such as toluene, xylene, butyl alcohol or surfactants, (2) by applying on the extract of microbial cells singly or in combination enzyme separation and purification means such as salting-out, isoelectric point precipitation, precipitation with an organic solvent, various chromatographic treatment, dialysis and others, or (3) further by applying on intact microbial cells, the extract of microbial cells or purified product thereof an immobilization means such as inclusion treatment, crosslinking treatment, adsorption treatment onto a carrier, etc.

Enzymatic reaction

Reaction substrates

The reaction substrates in the enzymatic reaction of this invention are 1,2,4-triazole-3-carboxamide and a ribose donor.

It is possible to use 1,2,4-triazole-3-carboxamide either in the free form or a salt form such as sodium salt.

In the present invention, the ribose donor means a ribose derivative capable of transferring the D-ribose residue to 1,2,4-triazole-3-carboxamide through the action of the enzyme source of the microorganism employed in the present invention, and it is inclusive, in addition to substances to be added as such, also of substances already contained as intracellular components in the microorganism cells to be used as an enzyme source, which may be either reaction substrates as such for the enzyme participating in the reaction of the present invention or precursor substances which can be converted into the above reaction substrate under the reaction conditions of the present invention. As such substances, there may be mentioned various ribonucleosides or D-ribose or various phosphoric esters of these.

The present invention encompasses utilization of a ribose donor contained in the enzyme source employed or produced in situ during the enzymatic reaction, but a preferred embodiment comprises the use of a ribose donor added from outside to the reaction system.

The ribose donor, as described above, can be any one of ribonucleosides or D-ribose or various phosphoric esters thereof. In other words, it is possible to use any ribonucleosides of which base moiety may be either of purine type or of pyrimidine type, and it does not also matter whether such a ribonucleoside may be derived either from a naturally occurring product or from a chemical synthesis. The phosphates of a ribonucleoside or D-ribose may have a monophosphate, diphosphate or triphosphate moiety at any one, two or all of the 2-, 3- and 5-positions. These phosphates may be either in the free form or conventional alkali salts such as of sodium, potassium, calcium, magnesium, ammonium, triethylammonium and the like. Typical examples of the ribose donor may include ribonucleosides such as inosine, adenosine, guanosine, xanthosine, uridine, and cytidine; ribonucleotides such as 5'-inosinic acid, 5'-adenylic acid, 5'-quanylic acid, 5'-xanthylic acid, 5'-uridylic acid, 5'-cytidylic acid, 2'(3')-inosinic acid, 2'(3')-adenylic acid, 2'(3')-guanylic acid, 2'(3')-xanthylic acid, 2'(3')-uridylic acid, and 2'(3')-cytidylic acid; and D-ribose, D-ribose-1-phosphate and the like.

The reaction substrate solution

The reaction substrate solution to be used for the enzymatic reaction of the present invention is basically an aqueous liquid comprising the aforesaid reaction substrates dissolved or suspended in an aqueous medium.

The aqueous liquid may optionally contain, in addition to the aforesaid reaction substrates, materials for promoting the enzymatic reaction, materials for improving solubility of the reaction substrates or materials for improving contact between the enzyme and the reaction substrates, such as phosphate ion donors, organic solvents, surfactants, metallic salts, coenzymes, acids, bases, sugars, etc.

The aqueous medium may be water or various buffers preferred for enzymatic reactions (e.g. phosphate buffers, imidazole-hydrochloric acid buffer, Veronal-hydrochloric acid buffer, Tris-hydrochloric acid buffer), which contains a phosphate ion donating source and may also contain various substances, if desired.

The enzymatic reaction in accordance with the present invention is catalyzed mainly by nucleoside phosphorylase, and thus requires the presence of phosphate ions in the reaction medium. A phosphate ion donating substance must thus be added to the enzymatic reaction medium when the medium is free of phosphate ions.

As the phosphate ion donating substance, there may be employed any compound dissociable into phosphate ion in an aqueous medium, such as phosphoric acid itself, inorganic phosphates such as salts of alkali metals, for example, sodium, potassium and the like, alkaline earth metals, for example, calcium, magnesium and the like or ammonium. Also, as the phosphate ion donating substances there may also be utilized systems capable of liberating phosphate ions in the solution for the enzymatic reaction such as combinations of various phosphoric esters employed with phosphatases, and combinations of the ribonucleotides with nucleotidases.

As the enzymes in such systems, there may be employed those contained in the enzyme source to be employed in the present invention, or alternatively enzymes or microbial cells or modifications of microbial cells having such enzymatic activities separately added. Such a phosphate donating system may be either added during the reaction from outside of the system or contained as a component in the enzyme source employed. That is, so long as they are in the form available for the enzymatic reaction, the above substances, either singly or as a system having two or more substances combined, or the microbial cells containing the above substances or modifications thereof may be separately added into the reaction mixture during the enzymatic reaction, or alternatively these substances contained as cellular components in the microorganism employed may also be used as such.

As the organic solvent, there may be employed, for example, methanol, ethanol, propanol, butanol, pentanol, acetone, methyl ethyl ketone, ethyl acetate, toluene, tetrahydrofuran, dioxane, dimethyl sulfoxide, dimethylacetamide, dimethylformamide, 2-methoxyethanol, 2-ethoxyethanol, and 1,2-dimethoxyethane.

Contacting method

The reaction of the present invention can be achieved by contacting the aforementioned enzyme source with the reaction substrates in an aqueous medium under non-proliferating conditions of the microorganisms concerned.

The contacting may be suitably selected depending on the form of the enzyme source employed. Usually, however, there may be employed a batch system in which an enzyme source is suspended or dissolved in a solution of reaction substrates and subjected to stirring or shaking preferably under heating, or reaction substrates are added into a suspension or solution of an enzyme source, or a continuous reaction system in which an enzyme source is optionally mixed with a suitable carrier, aid or adsorbent or immobilized thereon, and a solution of reaction substrates is continuously allowed to contact with the enzyme source.

Concentrations or amounts of reaction substrates and enzyme source

In carrying out the reaction, the substrate concentration in the reaction mixture is not particularly limited, but there is generally employed a substrate concentration below the saturated concentration of the substrate relative to the aqueous medium employed at the reaction temperature and it is also possible to increase the substrate concentration depending on the aforementioned solvent, surfactant and others added into the reaction substrate solution. The substrates may also be permitted to be present under a suspended state in amounts over saturated concentrations in the reaction mixture and the respective substrates dissolved therein as the progress of the reaction. During the reaction, substrates may be successively added into the reaction mixture to maintain their concentrations at appropriate levels. When substrates are to be dissolved, the substrate concentration for 1,2,4-triazole-3-carboxamide or a salt thereof may be generally about 5 to 200 mM, preferably 10 to 100 mM. As for a ribose donor, when it is to be separately added, its concentration may be generally about 5 to 300 mM, preferably about 10 to 150 mM.

The amount of an enzyme source employed can be easily determined by those skilled in the art according to preliminary experiments or others in view of the form of the enzyme source employed, the reaction efficiency as well as economy. However, in case of a batch system, for example in case of intact (wet) microbial cells, an amount of 10 to 150 mg/ml-substrate solution, or in case of dry microbial cells an amount of 2 to 30 mg/ml-substrate solution may be used. In a continuous reaction system, a suitable amount can also be set similarly as in case of the batch system.

The reaction conditions

The reaction conditions are not particularly limited except that the enzyme sources are subjected to the reaction under non-proliferating conditions, namely under the state where microbial cells concerned are dormant or dead.

As the method to subject the enzyme source under non-proliferating conditions for the reaction, there may be employed the method in which the enzymatic reaction temperature is set at a temperature range at which the microorganism employed cannot be proliferated (provided that the enzyme participating in the reaction of the present invention will not be inactivated at said temperature range), the method in which the microorganism cells are treated physically, chemically or biochemically as described above to make the microorganism non-proliferatable and thereafter provided for the reaction or the method in which a substance inhibiting proliferation of the microorganism employed such as toluene is added into the reaction substrate solution. These methods may be used either singly or in combination, but particularly among these methods, adjusting the reaction temperature is most effective and conveniently easy method.

In the reaction of the present invention, the reaction temperature is an important factor as described above and characterizes the present invention. While the reaction can proceed at a range from 37° to 80° C., but a range from 40° to 70° C. is practically preferred. The optimum temperature condition, which will vary depending on the reaction substrates employed, can readily be determined by those skilled in the art.

By carrying out the enzymatic reaction at a temperature over 40° C., the growth of the microorganism can be mostly inhibited. For example, the relation between the yield (%) of ribavirin from 1,2,4-triazole-3-carboxamide and the survival percentage of the microorganism employed after the reaction, when employing the intact cells of the same microorganism as used in Example 1 as hereinafter described and carrying out the reaction similarly at various temperatures of 28° to 60° C., is as shown in Table 1 below. The survival percentage of the microorganism is given in terms of the percentage of the living microorganism population/ml after the reaction based on that before initiation of the reaction.

TABLE 1

| Reaction temperature (°C.) | Ribavirin yield (%) | Survival percentage of microorganism (%) |
| --- | --- | --- |
| 60 | 75.25 | 0 |
| 50 | 71.82 | 0 |
| 45 | 55.95 | 0.19 |
| 37 | 28.01 | 2.13 |
| 28 | 0 | 91.30 |

As described above, the present reaction must be carried out under non-proliferatating conditions of the microorganism employed, namely under the conditions under which most of the cells of microorganism employed are dormant or dead.

Further, in the present invention, by setting the reaction temperature within the range as specified above, not only the rate of the enzymatic reaction producing ribavirin can be increased, but also the decomposition reaction of the ribavirin formed was experimentally confirmed to be suppressed. As an example, Table 2 shows the residual percentages (%) of ribavirin, when incubated at respective temperatures from 28° to 60° C. for 20 hours after adding one ml of a suspension of the intact cells of the same microorganism as employed in Examples 1 to one ml of a 20 mM ribavirin solution.

TABLE 2

| Reaction temperature (°C.) | Residual ribavirin percentage (%) |
| --- | --- |
| 60 | 100 |
| 50 | 100 |
| 45 | 100 |
| 37 | 92.80 |
| 28 | 90.14 |

From the above results, it can be confirmed that a reaction temperature of 45° C. or higher is preferred in this embodiment.

The reaction substrate solution may be maintained generally at pH 4 to 10, preferably pH 6 to 8 and, when pH is changed during the reaction, an acid such as hydrochloric acid, sulfuric acid or phosphoric acid or an alkali such as sodium hydroxide, potassium hydroxide, ammonia water or ammonia gas may be employed to correct pH to a preferable range.

The reaction time, which can be determined while confirming the conversion of the reaction substrates to a desired product, may be generally about 2 to 45 hours, preferably 24 to 36 hours in a batch system. In a continuous reaction system, the reaction may be carried out by setting appropriate conditions similarly as in a batch system.

Separation and purification

After the enzyme source may be removed by separation according to conventional procedures such as filtration, centrifugation or agglomeration separation, if desired, the reaction product is subjected to the step of separation and purification of ribavirin.

Separation and purification of ribavirin may be conducted according to known methods or modification thereof. For example, there may be employed conventional separation/purification methods, which may be used alone or in a suitable combination, such as various chromatographies, including ion-exchange chromatography, adsorption chromatography, partition chromatography, gel filtration, etc., the method utilizing partition between two liquid phases such as counter-current partition, counter-current extraction, etc. or the method utilizing the difference in solubility by concentration, cooling, addition of organic solvent, etc.

Analysis

In the present invention, analysis of ribavirin and 1,2,4-triazole-3-carboxamide was conducted by a high performance liquid chromatography. When analysis was carried out by use of the device and the conditions as shown below, ribavirin was eluted at around a retention time of 3.50 minutes, while 1,2,4-triazole-3-carboxamide at around a retention time of 2.65 minutes, and the respective quantities can be calculated from the calibration curves.

Device: Shimadzu High Performance Liquid Chromatograph Model LC-3A (manufactured by Shimadzu Corporation)

Column: Micro-BONDAPAK, $C_{18}$, 4.6 mm×250 mm (produced by Nippon Waters Limited)

Eluant: 20 mM Tris-hydrochloric acid buffer (pH 7.5) containing 2% acetonitrile

Flow rate: 1 ml/minute

Measurement wavelength: 225 nm

Operational column temperature: room temperature.

PREFERRED EMBODIMENTS

The present invention is described in more detail by referring to the following Examples, which are all illustrative of preferred embodiments of and not limitative of the present invention.

EXAMPLE 1

*Brevibacterium acetylicum* AT-6-7 was inoculated into 5 liters of a 2% aqueous solution of a powdery bouillon (produced by Kyokuto Seiyaku Kogyo Co., Ltd.) and shaking cultivation was carried out at 28° C. for 24 hours.

After completion of the cultivation, the cells were collected by centrifugation, washed and a sterilized water was added thereto to obtain 250 ml of a cell suspension. Into 750 ml of an aqueous solution containing 66.7 mM 1,2,4-triazole-3-carboxamide, 66.7 mM inosine and 100 mM monopotassium dihydrogen phosphate was added 250 ml of the above cell suspension, and the reaction was carried out at 60° C. for 24 hours (ribavirin yield: 74.88%).

Ribavirin yield refers to conversion (%) of 1,2,4-triazole-3-carboxamide into ribavirin.

The reaction mixture was subjected to centrifugation for removal of the microbial cells and then passed through a cation exchange resin (H+ form), and the passed solution and water washings were combined and applied on activated charcoal column. From the activated charcoal column, ribavirin was eluted with an ethanol-ammonia solution, and ethanol therefrom was passed through an anion exchange resin. The passed solution and water washings were combined, concentrated under reduced pressure to 50 ml and cooled. After cooling, the precipitated crystals were separated and dried to obtain 6.5 g of ribavirin crystals.

COMPARATIVE EXAMPLES

With the use of the same microorganism strain as in Example 1, production of ribavirin was attempted by adding a starting triazole compound during proliferation of the microorganism according to the same method as described in Example 1 of Japanese Patent Publication No. 17830/1979. Particularly, the microorganism strain was inoculated into 10 ml of a culture medium (pH 7.6) with a composition containing 130 g of glucose, 1 g of monopotassium dihydrogen phosphate, 3 g of dipotassium monohydrogen phosphate, 1 g of magnesium sulfate, 0.1 g of calcium chloride, 10 mg of ferrous sulfate, 5 mg of zinc sulfate, 10 mg of manganese sulfate, 5 mg of vitamin $B_1$, 10 mg of calcium pantothenate, 20 mg of cystine, 30 μg of biotin, 10 g of meat extract, 2 g of ammonium sulfate and 2 g of urea (separately sterilized) in one liter, and shaking cultivation was carried out at 28° C., while adjusting pH to 7.2 at every 12 hours with ammonia water. After 24 hours after initiation of the cultivation, 1,2,4-triazole-3-carboxamide was added at a concentration of 2 mg/ml, and cultivation was carried out for additional 4 days. The culture broth was subjected to centrifugation, and the supernatant was analyzed, whereby no formation of ribavirin was recognized at all.

EXAMPLE 2

The same microorganism strain as used in Example 1 was cultured similarly as in Example 1 (but each culture broth was 10 ml), and after cultivation cells were collected by centrifugation and each 1 ml of a sterilized water was added thereto to prepare a cell suspension.

To each cell suspension was added each 1 ml of an aqueous solution (pH 7.0) containing 20 mM 1,2,4-triazole-3-carboxamide, 20 mM of each of the various ribose donors as shown in Table 3 and 25 mM of monopotassium dihydrogen phosphate, and the reaction was carried out at 60° C. for 24 hours. After completion of the reaction, the cells were removed by centrifugation, and the supernatant was analyzed to obtain the results of ribavirin yield as shown in Table 3.

TABLE 3

| Ribose donor | Ribavirin yield (%) |
| --- | --- |
| Inosine | 75.66 |
| 5'-Inosinic acid | 73.23 |
| Adenosine | 59.30 |
| 5'-Adenylic acid | 70.82 |
| Guanosine | 76.15 |
| 5'-Guanylic acid | 67.16 |
| Cytidine | 88.60 |
| 5'-Cytidylic acid | 77.83 |
| Uridine | 85.19 |
| 5'-Uridylic acid | 83.93 |
| Ribose | 29.02 |
| Ribose-1-phosphate | 30.84 |

EXAMPLE 3

To each 100 ml of 2% bouillon medium was inoculated the same microorganism strain as used in Example 1, followed by shaking cultivation at 28° C. for 22 hours to obtain each cultured product of microbial cells. Then, each product was subjected to the following treatment to obtain respective suspensions of modifications of cells.

(1) Acetone-drying:

To intact microbial cells was added 50 ml of acetone, and the resultant mixture after being left to stand for 15 minutes was subjected to centrifugation. To the cells obtained was further added 50 ml of acetone and the same treatment was repeated, followed by vacuum drying to obtain dry microbial cells. Water was added to this product to obtain 10 ml of a suspension of the treated microbial cells.

(2) Freeze-thaw:

Intact microbial cells were freezed overnight at −80° C., then left to thaw and water was added to the thawed product to obtain 10 ml of a suspension of the treated microbial cells.

(3) Osmotic differential treatment:

To intact microbial cells was added 100 ml of a saturated aqueous sodium chloride, and the mixture after ice-cooling overnight was subjected to centrifugation. The supernatant was discarded and water was added to the microbial cells separated to obtain 10 ml of a suspension of the treated microbial cells.

(4) Sonic treatment:

Water was added to intact microbial cells to make up 10 ml, to which sonic treatment was applied at an output voltage of 1.6 KV for 20 minutes.

Each 10 ml of the above suspensions of the treated microbial cells and 10 ml of a suspension of untreated microbial cells obtained similarly as in Example 1 was admixed with each 10 ml of a reaction substrate solution (pH 7.0) containing 20 mM 1,2,4-triazole-3-carboxamide, 20 mM inosine and 25 mM monopotassium dihydrogen phosphate, and the reaction was carried out at 60° C. for 24 hours. Analysis of ribavirin yields gave the results as shown in Table 4.

TABLE 4

| Enzyme source, cells having undergone | Ribavirin yield (%) |
|---|---|
| Acetone-drying | 72.31 |
| Freeze-thaw treatment | 73.89 |
| Osmotic treatment | 71.50 |
| Sonic treatment | 70.11 |
| Untreated | 68.12 |

EXAMPLE 4

The same microorganism strain as in Example 1 was inoculated into 25 ml of a 2% bouillon medium and shaking cultivation conducted at 28° C. for 24 hours. After the cultivation, the cells were collected and water was added thereto to prepare cell suspensions each of 2.5 ml. To each suspension was added each 2.5 ml of the same reaction substrate solution as in Example 3, and the reaction was carried out at various temperatures (Table 5) for 20 hours and yields of ribavirin were analyzed to obtain the results as shown in Table 5.

TABLE 5

| Reaction temperature (°C.) | Ribavirin yield (%) |
|---|---|
| 28 | 6.1 |
| 37 | 27.3 |
| 45 | 48.0 |
| 50 | 59.6 |
| 55 | 71.5 |
| 60 | 81.1 |
| 65 | 82.8 |
| 70 | 33.8 |

EXAMPLE 5

With the use of the same microorganism strain as in Example 1, each 2.5 ml of microbial cell suspension was prepared similarly as in Example 4. To each suspension was added each 2.5 ml of the reaction substrate solution (A) or (B) as shown below, and the reaction was carried out at 60° C. for 20 hours. Analysis of the ribavirin yields gave the results as shown in Table 6.

Reaction substrate solution (A): 20 mM 1,2,4-triazole-3-carboxamide and 20 mM inosine;

Reaction substrate solution (B): 25 mM monopotassium dihydrogen phosphate was added to the same quantities of respective substrates as in the above reaction substrate solution (A).

TABLE 6

| Reaction substrate solution | Ribavirin yield (%) |
|---|---|
| (A) | 69.00 |
| (B) | 72.76 |

EXAMPLE 6

To 2.5 ml of the same microbial cell suspension as in Example 5 was added 2.5 ml of the reaction substrate solution (B) of Example 5, and the reaction was carried out at 60° C. for 20 hours, followed by separation of the microbial cells. To the cells separated was added 10 ml of water, and the resultant mixture was used for the next reaction. Thus, the same reaction as above was repeated 10 times. The relative ribavirin yields for respective reactions to that of the first reaction as 100 are shown in Table 7.

TABLE 7

| Repetition of reaction | Relative ribavirin yield |
|---|---|
| 1 | 100.00 |
| 2 | 96.33 |
| 4 | 94.37 |
| 6 | 88.10 |
| 8 | 88.02 |
| 10 | 88.00 |

EXAMPLE 7

Into one liter of a 2% bouillon medium was inoculated the same microorganism strain as in Example 1, and after shaking cultivation at 30° C. for 22 hours, the cultured product was subjected to centrifugation to obtain intact microbial cells.

To the microbial cells were added 20 ml of Liquid A [prepared by dissolving 24 ml of 1N-hydrochloric acid, 3.425 g of Tris and 0.23 ml of TEMED (N,N,N',N'-tetramethylethylenediamine) and diluting with water to 100 ml], 20 ml of Liquid B [aqueous solution prepared by dissolving 30 g of acrylamide and 0.8 g of BIS (N,N-methylenebis(acrylamide)) in water to be made up to 100 ml] and 40 ml of Liquid C [aqueous solution prepared by dissolving 0.3 g of ammonium persulfate in water to be made up to 200 ml], and the mixture was left to stand to effect immobilization of the cells. After immobilization, the product mass was disintegrated by means of a homogenizer to obtain 180 ml of immobilized microbial cells.

To 10 ml of the immobilized microbial cells. was added 20 ml of a reaction substrate solution (pH 7.0) containing 20 mM 1,2,4-triazole-3-carboxamide, 20 mM inosine and 25 mM monopotassium dihydrogen phosphate, and the reaction was carried out at 60° C. for 24 hours. The reaction mixture was analyzed to find that 62.89% of ribavirin was formed. When the reaction was carried out under the same condition by use of the intact microbial cells, the yield of ribavirin was 65.44%.

EXAMPLE 8

Respective microorganism strains as shown in Table 8 were inoculated to each 50 ml of the same bouillon medium as used in Example 1, and after shaking cultivation at 28° C. for 24 hours, cells were collected by centrifugation, followed by addition of a sterilized water to give each 5 ml of cell suspensions.

Each 5 ml of the above microbial cell suspensions was added to each 5 ml of an aqueous solution (pH 7.0) containing 20 mM 1,2,4-triazole-3-carboxamide, 20 mM inosine and 25 mM monopotassium dihydrogen phosphate, and the reaction was carried out at 60° C. for 24 hours. After the reaction was over, the ribavirin yield was analyzed to obtain the results as shown in Table 8.

TABLE 8

| Microorganism strain | Ribavirin yield (%) |
| --- | --- |
| *Brevibacterium imperiale* ATCC 8365 | 21.55 |
| *Corynebacterium equi* IAM 1038 | 35.17 |
| *Bacillus subtilis* ATCC 14593 | 10.64 |
| *Micrococcus varians* IFO 3765 | 26.56 |
| *Arthrobacter citreus* IFO 12957 | 11.97 |
| *Arthrobacter globiformis* IFO 12137 | 8.32 |
| *Micrococcus luteus* ATCC 4698 | 21.77 |
| *Micrococcus roseus* IFO 3768 | 11.18 |
| *Bacillus cereus* IAM 1029 | 3.30 |

EXAMPLE 9

Each of the various microorganism strains shown in Table 9 was inoculated to each 50 ml of an aqueous solution of a powdery bouillon and, after shaking cultivation at 28° C. for 24 hours, the cells were collected by centrifugation and a sterilized water was added thereto to prepare each 5 ml of cell suspensions.

To each 5 ml of an aqueous solution (pH 7.0) containing 20 mM 1,2,4-triazole-3-carboxamide, 20 mM inosine and 25 mM monopotassium dihydrogen phosphate was added each 5 ml of the above cell suspensions, and the reaction was carried out at 60° C. for 20 hours. After the reaction, the cells were removed by centrifugation, and analysis of ribavirin yields gave the results as shown in Table 9.

TABLE 9

| Microorganism strains | Ribavirin yield (%) |
| --- | --- |
| *Flavobacterium arborescence* IFO 3750 | 25.54 |
| *Flavobacterium lutescens* IFO 3084 | 76.26 |
| *Flavobacterium lutescens* IFO 3085 | 7.45 |
| *Microbacterium thermosphactum* IFO 12167 | 9.00 |
| *Xanthomonas oryzae* IFO 3312 | 69.25 |
| *Alteromonas putrefaceiens* ATCC 8071 | 11.68 |
| *Alteromonas putrefaceiens* ATCC 8072 | 47.35 |
| *Alteromonas putrefaceiens* ATCC 8073 | 21.14 |
| *Pseudomonas schuylkilliensis* IAM 1051 | 10.50 |
| *Pseudomonas ovalis* IAM 1002 | 11.11 |
| *Pseudomonas dacunhae* IAM 1089 | 7.98 |
| *Achromobacter parvulus* IFO 13182 | 27.84 |
| *Achromobacter xerosis* IFO 12668 | 51.84 |
| *Escherichia coli* IFO 3301 | 7.37 |
| *Escherichia coli* IAM 1268 | 61.47 |
| *Aerobacter aerogenes* IAM 1019 (FERM P-6538) | 12.18 |
| *Staphylococcus aureus* IAM 1011 | 18.61 |
| *Staphylococcus aureus* IFO 3060 | 18.25 |
| *Sarcina marginata* IAM 1130 (FERM P-6539) | 14.04 |
| *Bacterium succinicum* IAM 1017 (FERM P-6540) | 16.74 |
| *Serratia marcescens* IAM 1105 | 8.32 |
| *Proteus vulgaris* IAM 1025 | 11.88 |
| *Cellulomonas flavigena* IFO 3753 | 12.75 |
| *Cellulomonas flavigena* IFO 12680 | 22.10 |
| *Enterobacter aerogenes* IFO 12010 | 10.53 |
| *Enterobacter cloacae* ATCC 7256 | 12.18 |
| *Mycoplana bullata* IFO 13290 | 10.38 |
| *Vibrio anguillarum* IFO 13266 | 12.71 |
| *Erwinia carotovora* subsp. *carotovora* IFO 12380 | 11.98 |
| *Klebsiella pneumoniae* ATCC 8308 | 9.39 |
| *Aeromonas hydrophila* subsp. *anaerogenes* IFO 13282 | 16.16 |
| *Mycotorula japonica* OUT 6226 | 33.37 |
| *Candida polymorpha* IFO 0836 (FERM P-6541) | 23.15 |

EXAMPLE 10

*Pseudomonas putrefaceiens* ATCC 8072 was cultivated similarly as in Example 9 (but each culture broth was made 10 ml), and after the cultivation, cells were collected by centrifugation and each 1 ml of sterilized water was added thereto to obtain each cell suspension.

To each suspension was added each 1 ml of an aqueous solution (pH 7.0) containing 20 mM 1,2,4-triazole-3-carboxamide, 20 ml of various ribose donors as shown in Table 10 and 25 mM monopotassium dihydrogen phosphate, and the reaction was carried out at 60° C. for 20 hours. After the reaction, the microbial cells were removed by centrifugation and the supernatant was analyzed to give the results of ribavirin yields as shown in Table 10.

TABLE 10

| Ribose donor | Ribavirin yield (%) |
| --- | --- |
| Inosine | 49.16 |
| 5'-Inosinic acid | 39.06 |
| Adenosine | 34.65 |
| 5'-Adenylic acid | 30.80 |
| Guanosine | 54.70 |
| 5'-Guanylic acid | 46.94 |
| Cytidine | 62.77 |
| 5'-Cytidylic acid | 52.00 |
| Uridine | 72.20 |
| 5'-Uridylic acid | 73.42 |
| Ribose | 44.05 |

EXAMPLE 11

The reactions were carried out according to the same method as in Example 10 except that *Staphylococcus aureus* IAM 1011 and *Flavobacterium arborescens* IFO 3750 were employed and the nucleotides as shown in Table 11 were employed as ribose donors to obtain the results as shown in Table 11.

TABLE 11

| | Ribavirin yield (%) | |
| --- | --- | --- |
| Ribose donor | Sta. aureus IAM 1011 | F. arborescens IFO 3750 |
| 5'-Inosinic acid | 13.50 | 15.99 |
| 5'-Adenylic acid | 14.85 | 13.85 |
| 5'-Guanylic acid | 22.50 | 10.69 |
| 5'-Cytidylic acid | 10.60 | 14.79 |
| 5'-Uridylic acid | 18.29 | 18.74 |

EXAMPLE 12

*Flavobacterium lutescens* IFO 3084 was inoculated into 2 liters of a 2% aqueous solution of a powdery bouillon and shaking cultivation was carried out at 28° C. for 22 hours.

After the cultivation, the cells were collected and washed, followed by addition of a sterilized water to obtain 200 ml of a cell suspension.

The above cell suspension was added to 800 ml of an aqueous solution containing 50 mM 1,2,4-triazole-3-carboxamide, 75 mM inosine and 50 mM monopotassium dihydrogen phosphate, and the reaction was carried out at 60° C. for 24 hours to give a ribavirin yield of 72.55%.

After the reaction mixture was subjected to centrifugation to remove cells, the supernatant was concentrated under reduced pressure to 250 ml and cooled. After removal of hypoxanthine and inosine formed, the residual mixture was passed through a cation exchange resin (H+ form) and the passed solution and water washing were combined and applied on activated charcoal. From the activated charcoal, ribavirin was eluted with ethanol-ammonia solution. After ethanol was removed from the eluate, the residue was passed through an anion exchange column and the passed solution and water washings were combined and concentration under reduced pressure to 25 ml, followed by cooling. After cooling, the precipitated crystals were separated and dried to obtain 6.6 g of ribavirin crystals.

EXAMPLE 13

Various microorganism strains as shown in Table 12 were each inoculated into each 100 ml of a 2% aqueous solution a powdery bouillon, and after shaking cultivation at 30° C. for 22 hours, the cells were collected and water added to respective cells to prepare each 10 ml of respective cell suspensions.

Each of the above cell suspensions was added to each 10 ml of an aqueous solution (pH 7.0) containing 20 mM 1,2,4-triazole-3-carboxamide, 30 mM sodium uridylate and 25 mM monopotassium dihydrogen phosphate, and the reaction was carried out at 45° C. for 23 hours. After the reaction, cells were removed by centrifugation and ribavirin yields were analyzed to obtain the results as shown in Table 12.

TABLE 12

| Microorganism strains | Ribavirin yield (%) |
| --- | --- |
| Flavobacterium arborescene IFO 3750 | 26.98 |
| Alteromonas putrefaciens ATCC 8072 | 44.40 |
| Alteromonas putrefaciens ATCC 8073 | 18.62 |
| Escherichia coli IAM 1268 | 10.63 |
| Staphylococcus aureus IAM 1011 | 20.53 |
| Staphylococcus aureus IFO 3060 | 27.75 |
| Cellulomonas flavigena IFO 12680 | 67.65 |
| Enterobacter aerogenes IFO 12010 | 14.34 |
| Enterobacter cloacae ATCC 7256 | 10.42 |
| Vibrio anguillarum IFO 13266 | 19.76 |
| Erwinia carotovora subsp. carotovora IFO 12380 | 41.99 |
| Klebsiella pneumoniae ATCC 8308 | 9.69 |

EXAMPLE 14

Various microorganism strains as shown in Table 13 were each inoculated into each 50 ml of a 2% aqueous solution of a powdery bouillon and after shaking cultivation at 28° C. for 24 hours, the cells were collected and water added to respective cells to prepare each 5 ml of respective cell suspensions.

Each 5 ml of the above cell suspensions was added to each 10 ml of an aqueous solution (pH 7.0) containing 20 mM 1,2,4-triazole-3-carboxamide and 25 mM monopotassium dihydrogen phosphate, and the reaction was carried out at 45° C. for 24 hours. After the reaction, cells were removed by centrifugation and ribavirin yields were analyzed to obtain the results as shown in Table 13.

TABLE 13

| Microorganism strains | Ribavirin yield (%) |
| --- | --- |
| Brevibacterium acetylicum AT-6-7 FERM P-6305 (ATCC 39311) | 24.52 |
| Brevibacterium imperiale ATCC 8365 | 2.00 |
| Corynebacterium equi IAM 1038 | 10.40 |
| Bacillus subtilis ATCC 14593 | 2.25 |
| Micrococcus varians IFO 3765 | 1.83 |

EXAMPLE 15

Into 5 liters of a 1.5% yeast extract medium (pH 7.5) was inoculated 250 ml of a pre-culture of Brevibacterium acetylicum AT-6-7 (FERM P-6305 (ATCC 39311)), and cultivation was carried out at 28° C. for 24 hours. Microbial cells were recovered from the culture broth by centrifugation and made into 500 ml of a cell suspension.

To 500 ml of an aqueous solution (pH 7.0) containing 20 mM 1,2,4-triazole-3-carboxamide and 25 mM monopotassium dihydrogen phosphate was added 500 ml of the above cell suspension, and the reaction was carried out at 45° C. for 24 hours. Yield of ribavirin in the reaction mixture was found to be 24.38%.

The solution after removal of the microbial cells was treated with a cation exchange resin (H+ form) to remove unaltered 1,2,4-triazole-3-carboxamide, and then ribavirin in the treated solution was adsorbed on activated charcoal. After ribavirin was eluted with a 50% ethyl alcohol solution containing 2% ammonia, ethanol was evaporated and the residual solution was passed through an anion exchange resin (base form). The passed solution was concentrated to obtain 475 mg of ribavirin crystals.

What is claimed is:

1. A process for producing ribavirin which comprises reacting 1,2,4-triazole-3-carboxamide or a salt thereof with a ribose donor selected from the group consisting of ribose-1-phosphates, nucleosides and nucleotides in the presence of an enzyme source based on a microorganism belonging to the species Brevibacterium acetylicum containing an enzyme which catalyzes the reaction to form ribavirin, said reaction taking place at a temperature of 40°-80° C., such that said microorganism is essentially non-proliferative, said reaction being carried out in an aqueous medium under conditions effective to and for a time sufficient to form ribavirin therein and recovering ribavirin formed from said medium.

2. A process according to claim 1, wherein the ribose donor is added separately to said enzymatic reaction system.

3. A process according to claim 1, wherein the ribose donor is present in said enzymatic reaction system as a component contained in the enzyme source employed or as a metabolite of the microorganism during the enzymatic reaction.

4. A process according to claim 1, wherein the microorganism employed is Brevibacterium acetylicum AT-6-7.

5. A process according to claim 1, wherein the enzyme source is selected from the group consisting of cultures of microorganisms, intact cells of microorganisms, and modifications of cells of microorganisms.

6. In a process for producing ribavirin from 1,2,4-triazole-3-carboxamide and a ribose donor in the presence of an enzyme source, the improvement comprising the use of an enzyme source capable of catalyzing the reaction between 1,2,4-triazole-3-carboxamide and a ribose donor, said enzyme source, being based on the microorganism of a species of Brevibacterium acetylicum.

7. A process as claimed in claim 6 in which the microorganism is Brevibacterium acetylicum AT-6-7 or a microorganism derived therefrom.

* * * * *